Figure 27:
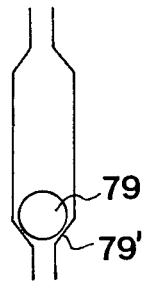

United States Patent [19]

Oehler et al.

[11] Patent Number: 4,557,603
[45] Date of Patent: Dec. 10, 1985

[54] DETECTION MEANS FOR THE SELECTIVE DETECTION OF GASES, BASED ON OPTICAL SPECTROSCOPY

[76] Inventors: Oskar Oehler, Streulistrasse 24, Zürich; Alexis Fries, In der Lachen 11, Dietikon, both of Switzerland

[21] Appl. No.: 438,897
[22] PCT Filed: Feb. 23, 1982
[86] PCT No.: PCT/CH82/00026
§ 371 Date: Oct. 25, 1982
§ 102(e) Date: Oct. 25, 1982
[87] PCT Pub. No.: WO82/02950
PCT Pub. Date: Sep. 2, 1982

[30] Foreign Application Priority Data

Feb. 25, 1981 [CH] Switzerland ............ 1266/81
Mar. 26, 1981 [CH] Switzerland ............ 2058/81
Jul. 24, 1981 [CH] Switzerland ............ 4853/81
Oct. 29, 1981 [CH] Switzerland ............ 6901/81

[51] Int. Cl.$^4$ ............................ G01N 21/17
[52] U.S. Cl. ............................ 356/418; 356/51; 250/343
[58] Field of Search ............ 250/343–345; 356/51, 300, 432, 436, 437, 440, 418

[56] References Cited

U.S. PATENT DOCUMENTS 3,562,524  2/1971  Moore et al. ............ 250/343
3,946,239  3/1976  Salzman et al. ............ 250/461.2
4,188,543  2/1980  Brunsting et al. ............ 356/318

Primary Examiner—F. L. Evans
Attorney, Agent, or Firm—Roylance, Abrams, Berdo & Goodman

[57] ABSTRACT

An optical detection system for selectively detecting gases comprises a light source emitting light thermally or mechanically modulated and supplied to a measuring cell. The light source includes an emitter enclosed in an ellipsoid reflector. The ellipsoid reflector can receive measuring gas directly, or is evacuated or filled with an inert gas which does not absorb in the measuring gas absorption range. With measuring gas supplied directly to the reflector, the light emanating from the reflector is supplied to a wide-band detector, combined with a monochromator, e.g. an optical narrow-band filter. With an evacuated or inert gas filled reflector, after traversing a monochromator, the light is irradiated into a photoacoustic detection cell containing the measuring gas. The photoacoustic cell is completely or approximately closed during measurement. Devices, providing the acoustic decoupling in the photoacoustic cell during the measurement and gas exchanges, can include capillaries in the cell wall, liquid cutout devices, mechanical valves or diaphragm pump-valve combinations. Microphone signals processed by a lock-in amplifier operating in a digital off-line manner and controlled by a microprocessor can control the system. The gas scavenging and signal processing of several gas detector units can take place with a single processor unit.

21 Claims, 31 Drawing Figures

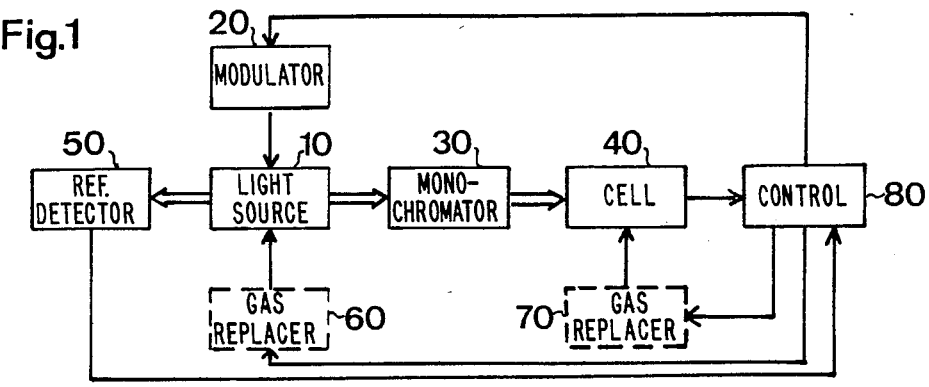
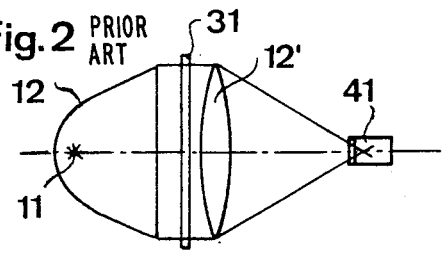
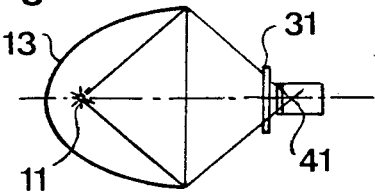
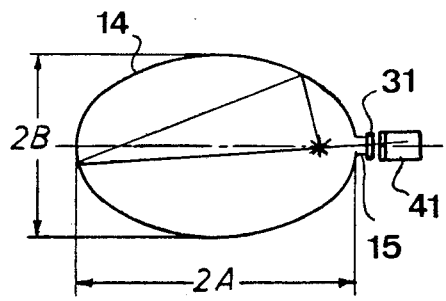
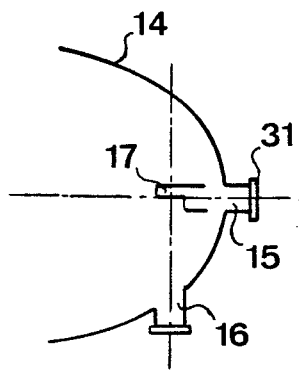
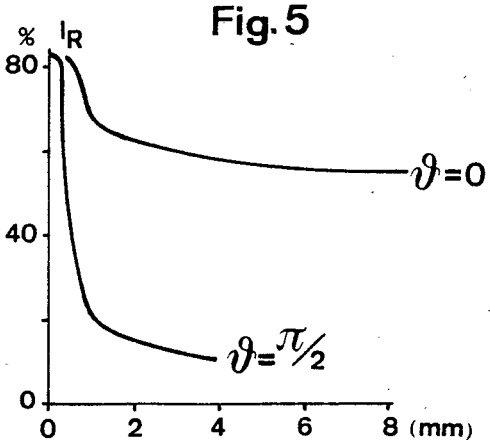

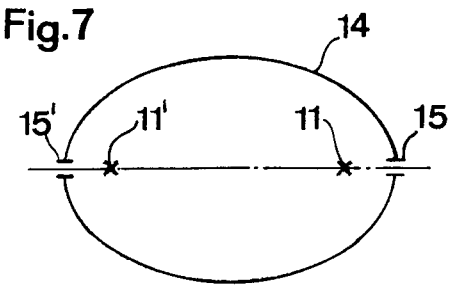
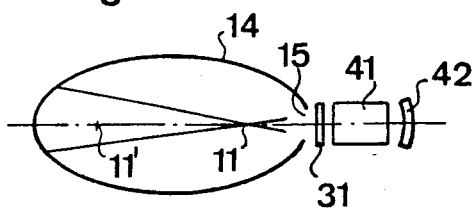
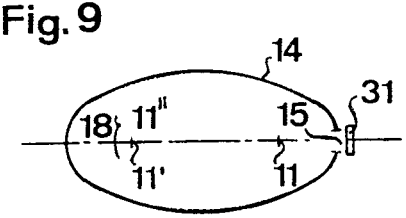
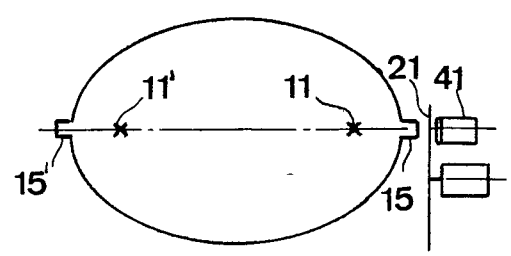
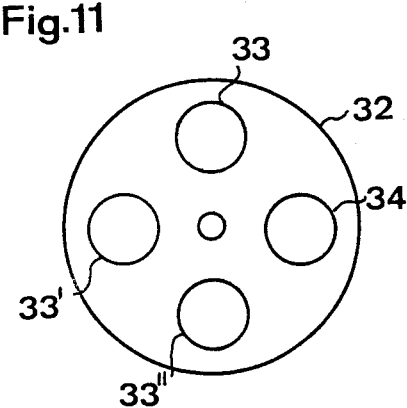
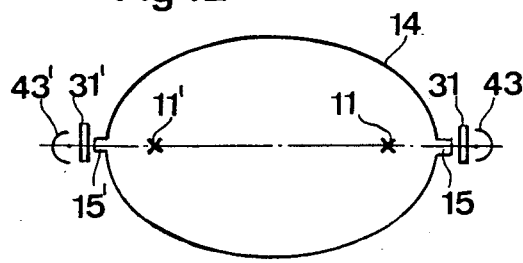
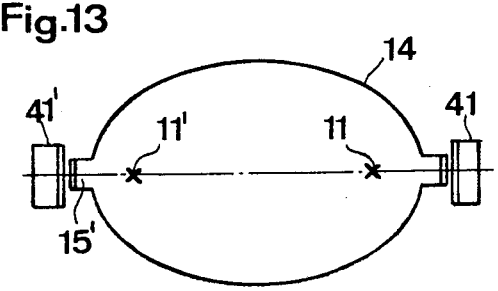
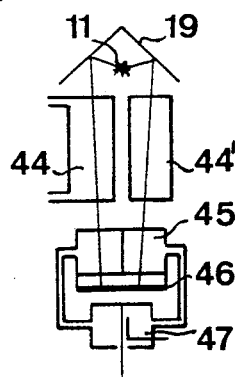

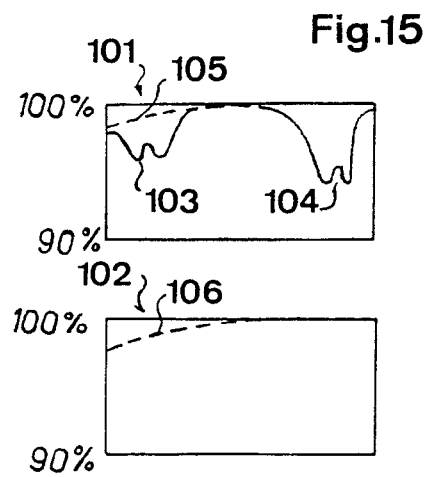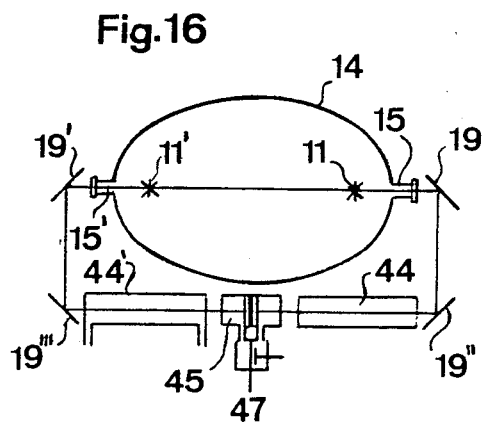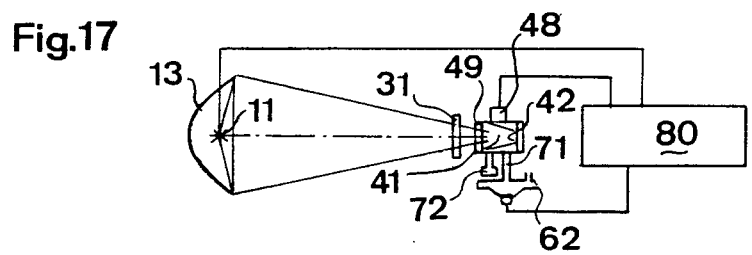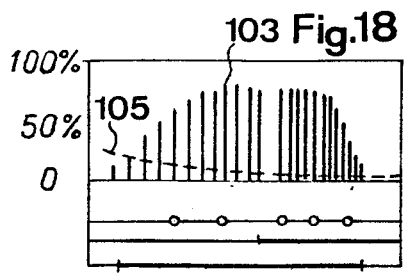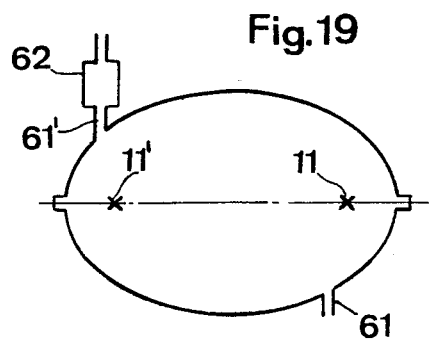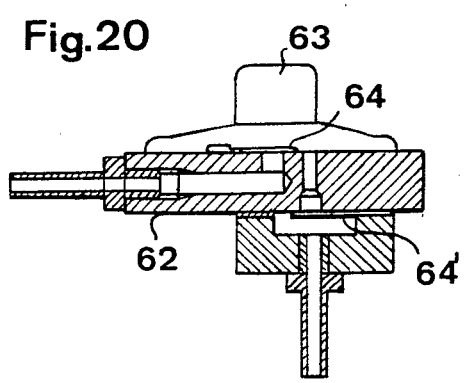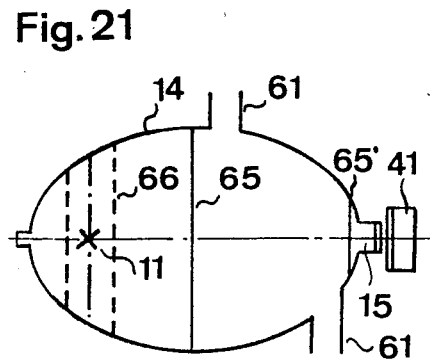

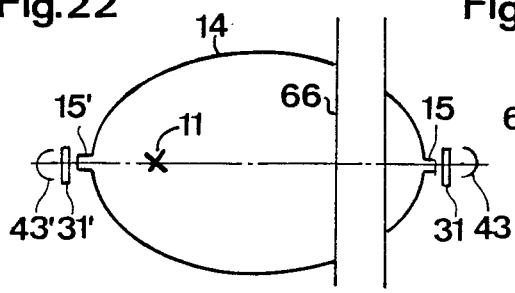
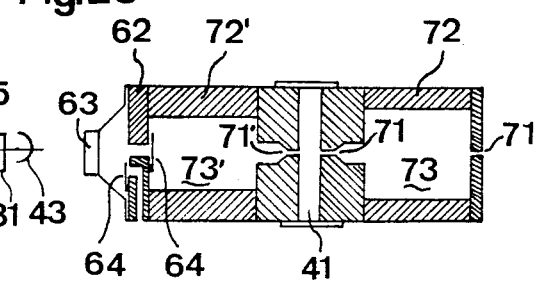
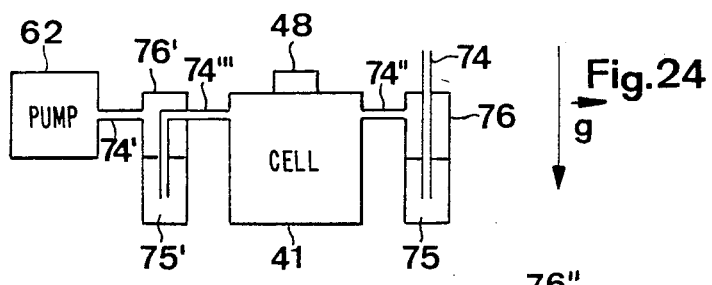
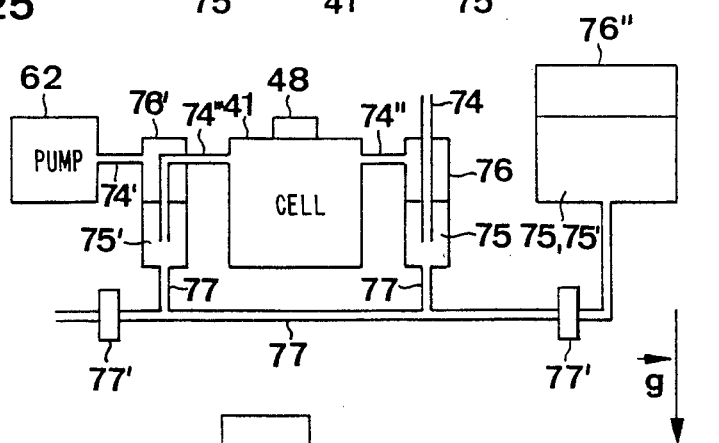
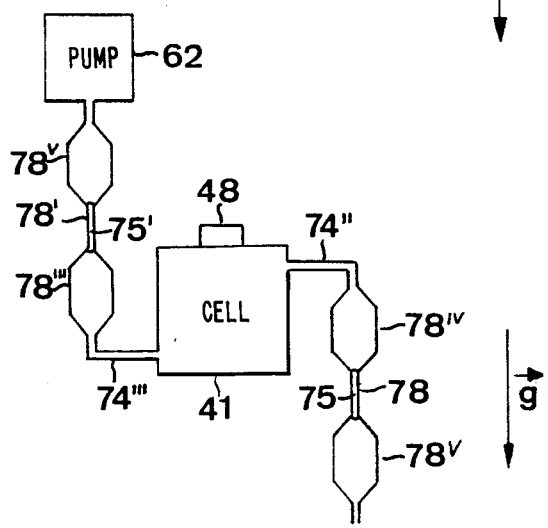

DETECTION MEANS FOR THE SELECTIVE DETECTION OF GASES, BASED ON OPTICAL SPECTROSCOPY

The invention deals with the field of optical spectroscopy, as well as geometrical optics. It relates to a relatively uncomplicated detection means for the selective detection of gases. The detection means essentially comprises a thermally or mechanically modulated incandescent body arranged in an almost closed ellipsoid reflector and whose light is supplied to a detection cell. The ellipsoid reflector either directly contains the gas to be measured or it is evacuated or filled with an inert gas which is non-absorptive in the measuring gas absorption range. In the former case, the light emanating from the ellipsoid is supplied to a wide-band detector combined with a narrow-band interference filter or a narrow-band detector. In the latter case of the non-light-absorbing ellipsoid filling, after passing through a narrow-band interference filter, the light is irradiated into a measuring gas-containing photoacoustic cell. In this case, measurement takes place with the photoacoustic cell completely or almost completely closed. Acoustic decoupling during measurement and the exchange of the gas in the photoacoustic cell can be ensured by capillaries in the cell wall, liquid barriers, or gravitation-controlled ball valves together with a gas supply device, which is in turn based on a small loudspeaker, or by a cut-off delivery device comprising a combination of diaphragm pumps and disk valves.

The microphone signal is detected and processed by means of a lock-in amplifier operating in a digital off-line manner and which is controlled by a microprocessor. A single processor unit can control in parallel or in series the gas scavenging and signal processing of a plurality of detection units.

The production of an almost parallel light beam from light irradiated by an almost punctiform light source is known from the general teachings of geometrical optics. In general, parabolic or spherical mirrors and/or spherical or aspherical lens systems, i.e. optical condensers are used for this purpose. If interest is attached to a high radiation efficiency of the light source and if the light beam is also to have a small divergence, it is indispensible to have large geometrical dimensions of the optical system producing the light bundle. In the construction of optical spectrometers, this is disadvantageous and of decisive importance. Thus, a good resolution requires on the one hand in the case of the conventionally used dispersion or interference monochromator systems a small divergence of the bundled light beams at the monochromator (this requirement also applies when using a narrow-band interference filter) and on the other hand every effort is generally made to ensure that the maximum proportion of the radiation from the light source can be used.

In the case of infrared spectrometers, account must be taken of the atmospheric absorption in the beam path, particularly due to water vapour, this more particularly being achieved by scavenging with dry air or evacuating the complete unit. Thus, for these reasons alone, in certain applications there is a desire for an optical system which, with small geometrical dimensions, supplies an intense light beam with small divergence.

The requirements regarding divergence are not too high when using interference filters. To avoid an undesired change to the band pass characteristics of the interference filter, half the angular opening of the light bundle should be below 15 angular degrees. Even when the unit is not closed, it is desirable for the aforementioned reasons for the light beam to be guided over the minimum distance through the surrounding atmosphere. These requirements are only inadequately fulfilled by conventional light/condenser systems.

It is certainly necessary for the light source to be intensity-modulated and this is generally carried out mechanically by means of a rotary sector disk. Since, however, inexpensive detectors (e.g. pyroelectric elements or photoacoustic cells) are often operated in optimum manner at low frequency, the light source can often be directly thermally modulated without any need for a light interrupter. This solution is particularly favourable for a simple and reliably operating gas detection system.

Particular importance is attached to carbon dioxide in gas detection. On the one hand, it can hardly be detected with limited expenditure, because the inexpensive, proven metal oxide semiconductor sensors do not respond to $CO_2$, whilst on the other hand, e.g. the quality of the air in the air conditioning systems or the occurrence of fires can be evaluated by the detection of the $CO_2$ content in the air. $CO_2$ very strongly and specifically absorbs infrared light. Thus, the optical determination of $CO_2$ is very obvious and is frequently used. The relatively high $CO_2$ concentration in the air and the high absorption coefficient do not, however, make it absolutely necessary to use the highly sensitive, optoacoustic method. Thus, it is sufficient to carry out an extinction measurement, i.e. a determination of the light attenuation in the test gas. However, with such a measurement, it is absolutely necessary for the intensity of the light beam to be very accurately known before entering the absorption cell, because the concentration determination takes place on the difference of the light intensity of the wavelength specific to the gas before and after the light absorption path. It is therefore conventional practice to couple out part of the light by auxiliary optics, e.g. a partly reflecting mirror, but this involves additional material and adjusting expenditure.

To ensure a long light path and consequently to achieve a considerable attenuation of the beam, despite limited dimensioning of the measuring device, cells are often used for extinction measurements of gases in which the light is reflected backwards and forwards a number of times and they are called multiple reflection cells. In the case of such a cell, it is on the one hand necessary for the incident light beam to be narrowly bundled (it being possible to counteract the divergence of the beam by a special mirror shape) and on the other hand the mirror system must be very accurately adjusted. Multiple reflection cells are consequently usually very complicated and costly. An important disadvantage of multiple reflection cells is the ageing of the optical system, i.e. the light reflectivity varies over a period of time and the geometry becomes misadjusted. Such changes lead to intensity attenuations which, unless calibration measurements are frequently carried out, cannot be differentiated from the signal attenuation caused by the test gas.

The photoacoustic gas detection method has proved very satisfactory in detecting low concentration, atmospheric gas impurities, such as e.g. carbon monoxide, nitric oxide or methane. This method consists of determining by means of a microphone the pressure changes also occurring in a gas mixture when monochromatic light (mainly infrared radiation) is absorbed by a gas component, cf the article by L. G. Rosengren, Applied Optics, Vol. 14, p. 1960, 1975. For this purpose, in general intensely tunable infrared lasers, together with highly sensitive condenser microphones are used.

The fact that the main constituents of air, i.e. nitrogen, oxygen and argon, within the scope of dipole approximation, absorb no infrared radiation, has a favourable effect. For example, L. B. Kreuzer was able to detect a 16 mW laser methane in nitrogen, corresponding to a concentration of 10 ppb ($10^{-8}$), cf J. Appl. Physics. Vol. 42, p. 2934, 1971. It has also been postulated that when using intense infrared laser radiation, concentrations up to $10^{-13}$ can be measured.

The detection system can be considerably simplified with the reduced demands on the sensitivity of the gas detection. In particular, the costly tunable infrared laser can be replaced by a simple system comprising an incandescent body and a narrow-band interference filter. Recently, M. J. D. Low and G. A. Parodi in Infrared Physics, Vol. 20, p. 333, 1980 described an infrared spectrometer based on the optoacoustic effect, in which an incandescent material is used in place of a laser. However, in combination with a grating monochromator, this source did not prove satisfactory for an optoacoustic infrared spectrometer, due to its intensity attenuation. From the intensity standpoint, the replacement of the grating monochromator by an interference filter leads to advantages, but at the cost of flexibility and accuracy.

In one category of gas analyzers, based on the photoacoustic effect, the infrared laser has been successfully replaced by an incandescent body. This involves the so-called, non-dispersive, photoacoustic gas analyzer systems, of which many different constructions are known. Reference is made in this connection e.g. to DAS No. 2,751,047 by O. H. Blunck and DOS No. 2,728,089 by U. Deptolla and W. Fabinski. In such non-dispersive systems, the quantity of light absorbed by the gas component adapted to the filter does not directly give rise to the microphone signal and instead the difference in the light attenuation between test gas and a reference gas is selectively measured. The gas-selective light intensity difference measurement is determined by means of a photoacoustic difference measuring cell filled with the gas of the component under investigation. This leads to the important advantages that no monochromatic light source is required and that on changing to detection of another gas, it is only necessary to replace the corresponding gas filling in the photoacoustic cell, or the cell itself. However, such systems have a complicated construction, because in conjunction with the difference signal measurement the light beam must be split and the two components very accurately equalized.

Photoacoustic cells are successfully used both in acoustic resonance and in non-resonance. In the case of an optoacoustic cell operated in acoustic resonance, the cell can be kept open during the measurement, if the opening takes place in nodes of the acoustic resonator. In the case of non-resonance, where working takes place in low modulation frequencies of the light, it is indispensible to keep the cell closed during the measurement. The pressure rise in the cell as a result of light absorption is continuously compensated by a large opening in the wall, which means that the photoacoustic effect is attenuated or even prevented. In addition, the opening couples atmospheric pressure fluctuations into the cell (space noise). This could make the measurement very difficult or even impossible. This problem does not occur in non-dispersive, photoacoustic systems, because there the cell with the measuring gas is separate from the photoacoustic detection area.

In the case of the photoacoustic effect, which is based on the infrared radiation being absorbed by the gas being tested, the weak radiation absorption on the photoacoustic cell walls has a disadvantageous effect, cf the Article by L. B. Kreuzer in J. Appl. Physics, Vol. 42, p. 2934, 1971. On limiting to a gas concentration detection limit in the ppm range ($10^{-6}$), the light reflection on the cell wall can lead to advantages in that the light passes through the cell a number of times, so that the size of the light path is increased. Such so-called photoacoustic multiple path cells have been successfully used e.g. by R. D. Kamm, J. Appl. Physics, Vol. 47, p. 3550, 1976 in the detection of n-butane in nitrogen.

As correct gas concentration determination makes it necessary for the cell to be well scavenged prior to the measurement, an alternating scavenging-measuring process is indispensible for the case of an identical test gas and detection cell.

The microphone or light detector signal has an alternating fraction with the periodicity of intensity-modulated light striking the photoacoustic cell. According to the prior art, lock-in amplifiers are used for detecting this signal. These consist of devices which filter and amplify from a signal that fraction which has the same frequency as the reference signal and which is also in phase relationship therewith. Equipment of this type is available on the market in a number of forms.

Under the presently prevailing conditions of a very low modulation frequency below 15 Hz and the possibility that the incandescent body can be controlled by a reference signal internally produced by the lock-in amplifier, advantages result from a digitally functioning apparatus controlled by a microcomputer as compared with conventional, known constructions. Reference is made in this connection to one of the few descriptions of a digitally operating lock-in amplifier by S. Cova and A. Longoni in Rev. Sci. Instrum., Vol. 50, p. 296, 1979. These are devices operating in an on-line manner, i.e. circuits in which signal processing takes place in a continuous manner. In our case of an alternating gas change and measuring process, the stabilization time of an on-line apparatus prior to the measurement, which can represent a multiple of the time constant, would require a correspondingly low measuring rate. Apart from the detection and processing of the microphone signal, it is necessary to monitor the gas change, a task which can be very easily performed by a microcomputer.

The problem of the invention is to avoid the aforementioned disadvantages and provide an inexpensive, flexible and selective gas detection system, based on the principles of optical spectroscopy. This gives rise to the following partial problems:

Provision of an optical device having small geometrical dimensions, which, with only limited adjustment requirements, makes it possible then in the case of an optimum light output of the light source to produce a light beam having a small cross-section and small divergence in a system which is completely, partly or not closed with respect to the atmosphere.

The optical device is to be constructed in such a way that its light emissivity can be determined.

The optical device must be so constructed that it is suitable for mass detection.

Another problem involves producing a device in such a way that the measuring gas can be interchanged. When using photoacoustic gas measurement cells, the device must simultaneously ensure the acoustic decoupling of the cell.

The problem is solved by the arrangement of at least one small incandescent body, e.g. a coil, in one of the two focal points of a completely or partly closed rotating ellipsoid reflector and a decoupling of the measurement bundling of rays formed by an opening in the direction of the extended main axis of the ellipsoid. The reference bundle of rays is decoupled by an additional opening in the opposite direction of the extended main axis of the ellipsoid.

The modulation of the incandescent body can be produced thermally or mechanically with the aid of a rotary sector disk. The monochromator is constituted by at least one optical narrow-band-pass filter, preferably an interference filter. However, several optical filters can be arranged on a rotary disk, which e.g. simultaneously fulfils the function of the light modulator.

A detector not functioning in gas selective manner, e.g. a pyroelectric element, or a photoacoustic measuring cell containing the measuring gas is used for light measurement purposes.

In the latter case, the efficiency of the gas detection can be improved by fitting a mirror to the back of the photoacoustic cell.

As the cell is operated in acoustic non-resonance and at low frequency, prior to detection it must be scavenged with the measuring gas. This takes place through narrow capillaries in the cell wall or by using a non-linear flow system, based on hydrodynamic principles, whose operation can be likened to that of a Schmitt trigger.

A feed device essentially based on a small loudspeaker with a plastic diaphragm onto which aluminium is evaporated is used for the forced gas circulation.

The microphone signal is detected and processed by means of a digital lock-in amplifier operating in an off-line manner and based on a microcomputer. This also controls the exchange of the gas in the optoacoustic cell and any change to the interference filter, together with the light source modulation during the measurement. Using a single microcomputer system, a plurality of detection cells can be simultaneously or sequentially controlled and their output signals processed.

The invention is described in greater detail hereinafter relative to non-limitative embodiments and the attached drawings, wherein show:

FIG. 1 a survey of the functional components of the gas detector.

FIG. 2 a prior art parabolic reflector with a light source in the focal point.

FIG. 3 a prior art ellipsoid semireflector with a light source in the focal point.

FIG. 4 an ellipsoid reflector according to the invention with a light source in one of the two focal points and light coupling out in the direction of the large main axis.

FIG. 5 characteristics of the intensity transfer of the ellipsoid reflector of FIG. 4.

FIG. 6 a detail of the embodiment of FIG. 4 with a suspension of an incandescent coil, the measures for coupling out the light, as well as a connection for evacuating a reflector and adjusting the coil.

FIG. 7 sketches of the ellipsoid reflector according to FIG. 4 with coupling out of the measuring and reference beam.

FIG. 8 a further embodiment of the ellipsoid reflector of FIG. 4.

FIG. 9 a further embodiment of the ellipsoid reflector of FIG. 4.

FIG. 10 the ellipsoid reflector with a mechanical light interrupter in the measuring beam.

FIG. 11 a possible embodiment of a combined monochromator-light interrupter.

FIGS. 12 and 13 the ellipsoid reflector with coupling out of the measuring and reference signal and arrangement of detector cells.

FIG. 14 selective non-dispersive photoacoustic gas analyzer according to the prior art.

FIG. 15 attenuation of the test and reference beam in the non-dispersive optoacoustic gas analyzer.

FIG. 16 use of the ellipsoid reflector for non-dispersive gas analysis.

FIG. 17 survey of the selective gas sensor system according to the invention.

FIG. 18 infrared spectrum of carbon monoxide, the interference by water also being shown.

FIG. 19 the ellipsoid reflector cell with measuring gas replacement device.

FIG. 20 feed device for gas change.

FIGS. 21 and 22 ellipsoid reflector cell with separate light source part.

FIG. 23 photoacoustic cell with gas replacement by capillaries.

FIG. 24 photoacoustic cell with acoustic liquid cutoff.

FIG. 25 construction according to FIG. 24 with additional liquid replacement device.

FIG. 26 photoacoustic cell with acoustic cutoff by means of liquid-filled capillaries.

FIG. 27 ball valve for acoustic cutoff.

Figure 28:
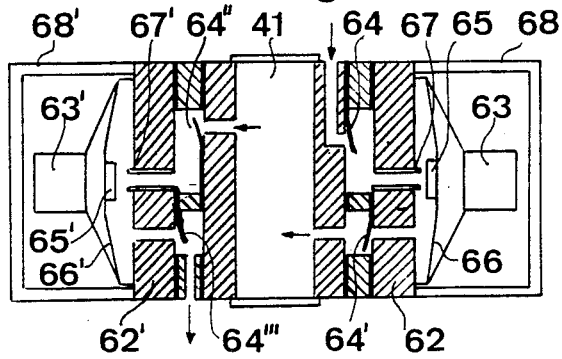

FIG. 28 photoacoustic cell with combined gas replacement-cutoff device.

Figure 29:
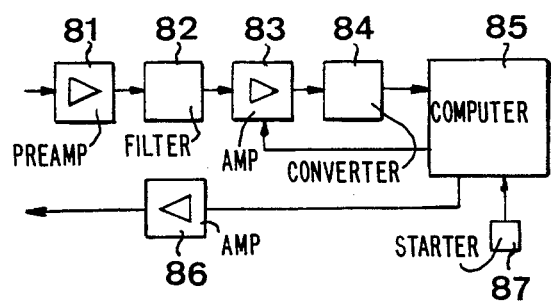

FIG. 29 block diagram of the hardware of the digital lock-in amplifier.

Figure 30:
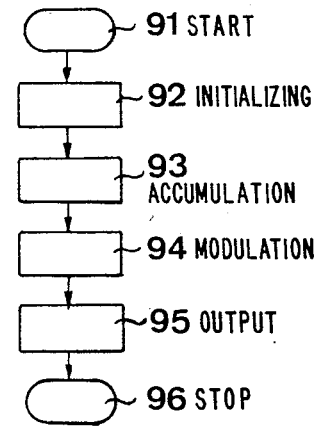

FIG. 30 flow chart of the digital lock-in amplifier.

Figure 31:
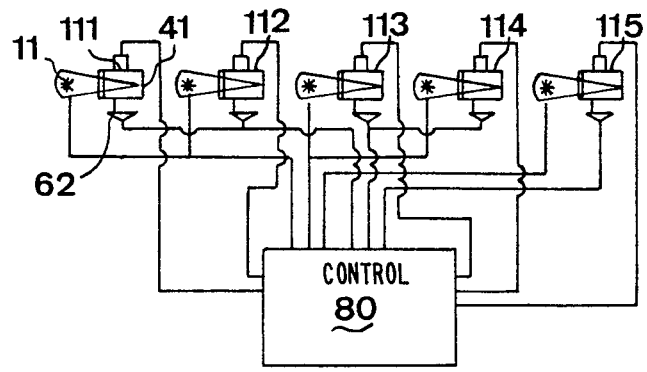

FIG. 31 gas detection system with several optoacoustic cells.

FIG. 1 is an overall view of the functional components of the gas detector. The radiation emanating from the light source 10 and intensity-modulated by the light modulator 20 is, after passing through the monochromator, supplied as the measuring beam to the measurement detector cell 40 and is also supplied possibly as a reference beam to reference detector 50. The test gas is either located in light source 10, where it is replaced with the aid of the gas replacement device 60, or in the measurement detector cell 40, which is in this case constructed as a photoacoustic cell. In the latter case, the gas replacement device 70 is responsible for gas replacement before the measurement and for acoustic decoupling of the cell during the measurement. The electric signals of detector cell 40 and possibly reference detector cell 50 are detected and processed by the evaluation and control device 80. Furthermore, this device controls the light modulator 20, the gas replacement device 60 or 70 and possibly monochromator 30. The individual components will be described in detail hereinafter.

By means of FIGS. 2 and 3, reference will be made to the previously described prior art in connection with light source 10.

The invention is based on the following fact. According to the laws of geometrical optics, a light beam emanating from the focal point 11 of an ellipsoid according to FIG. 4, following a reflection on the reflector wall, passes into focal point 11' (and vice versa).

On following such a light beam, it can be established that with an increasing number of reflections on the reflector wall, it comes ever close to the large main axis and after only a few reflections substantially coincides therewith.

A light source provided in one of the two focal points therefore produces a very intense and in the ideal case parallel light bundle in the large main axis.

This light bundle can be coupled out by a small opening in one of the intersection points between the large main axis and the ellipsoid surface (e.g. at 15 in FIG. 4). However, the width of the opening has the secondary effect that a beam can leave the reflector system before striking the large main axis. This leads to the formation of a light cone at the ellipsoid opening, whose opening angle is determined on the one hand by the diameter of the opening and on the other by the ellipsoid parameters.

The use of closed ellipsoidal reflectors is not novel. Such mirrors are occasionally used when it is a question of supplying light from a small source to a small sample with high efficiency. However, what is novel is the utilization of the collecting property of the light along the large main axis and the coupling out of the radiation in the extension of this axis. A patent application was filed in Switzerland for this device on Feb. 25, 1981, (No. 1 266/81-0).

It is not surprising that this method is not used, because it is completely useless for most optical applications, i.e. whenever it is a question of representing a source as accurately as possible or producing a precise parallel beam. High accuracy of beam guidance is prevented by the fact that the individual light beams leave the ellipsoid after a different number of reflections. When using a filter-monochromator provided, high demands do not have to be made on the convergence of the light beam and the distance from the light cutout detector can be kept small.

However, this device does not in fact function in the ideal case, i.e. when the light source with optimum emissivity is precisely punctiform and is located precisely in a focal point of a fault-free ellipsoid. All light emitted by the source is reflected back onto it after two reflections and absorbed. However, it is realistic to use a spiral light source with a considerable transparency and negligible dimensions. The light reflected back onto the coil is not lost and in fact brings about an additional heating of the incandescent body.

The filter 31, which can now be kept small, is located in the vicinity of opening 15 and the detector cell is positioned immediately behind it.

Calculations with the aid of a computer simulation have revealed that in the case of a reflectivity of the ellipsoid inner surface 14 of 95% for the case where a punctiform light source is located in focus 11, 84% of the light radiated by coil 17 leaves the 1 cm wide exit port 15 after a small number of reflections at an angle to the large main axis of max. 9.8°. 53% of the emanating light beams are located within a cone with a 3° half opening angle (the ellipsoid semiaxes are assumed to have a length of 7.2 and 6 cm).

The computer simulation also revealed that on deviating the position of the light source out of the focal point, there was a considerable drop in the light output, mainly in the direction perpendicular to the large main axis (cf FIG. 5, $\theta = \pi/2$: direction perpendicular to the large main axis). FIG. 5 shows the intensity transfer as a function of the deviation of the light sources on focal point 11.

Whilst taking account of these facts, the computer calculation gave a total intensity transfer of 56% for a 2 mm filament located in the large main axis.

The results obtained by computer simulation were very satisfactorily confirmed experimentally on a reflector with the indicated dimensions.

As stated, there is a drop in the light output of the device according to the invention if the light source is located outside the associated focal point in the ellipsoid. Thus, a good adjustment or centering of the light source is important. This requirement can e.g. be very easily filfilled if the connection 16, as shown in FIG. 6, used for evacuation or gas filling is positioned in such a way that its longitudinal axis is directed towards the focal point. If parallel light is irradiated through opening 15 along the large main axis, a large part thereof is focused in the focal points. Thus, a coil 17 located in a focal point is illuminated as soon as it is correctly adjusted.

As stated hereinbefore, there is a considerable reduction in the light output mainly in the perpendicular direction ($\theta = \pi/2$) to the large main axis. As it cannot be excluded that the position of the incandescent body relative to the focal point 11 will change over a period of time and in addition the reflectivity of reflector 15 is e.g. subject to changes due to dirtying, it is well worth performing a reference measurement.

This problem can be solved in that e.g. a reference beam is coupled out of the ellipsoid reflector by a second opening 15' facing opening 15 and located e.g. on the large main axis, cf FIG. 7.

This arrangement makes it possible to largely eliminate changes to the light output of the device resulting from the geometry because, as a result of the multiple reflections, the light intensity at 15 is approximately proportional to that at 15'. This applies even if there is no light source or a light source of different intensity to that at focal point 11 at focal point 11'.

However, it is pointed out that the second opening 15' in ellipsoid 14 leads to an attenuation of the light intensity for small emergence angles compared with the construction with a single opening 15.

The invention can also be supplemented in the following manner:

(1) According to FIG. 8:

In order to reduce the aforementioned secondary effect of opening 15, at the end of cell 41 is fitted an elliptical reflector 42, having the same focal points as reflector 14 (42 is possibly approximatable by a spherical reflector). As a result, the beams passing through 41 are reflected back onto the two focal points 11 and 11', so that more beams fall in the large main axis, so that a more optimum realisation of the aforementioned effect is obtained.

(2) According to FIG. 9:

Within the ellipsoid, a spherical or parabolic reflector 18 is fitted in such a way that its focus coincides with one of those of the ellipsoid, e.g. 11' and its axis is located in the ellipsoid axis.

This reflector reduces the number of reflections in the ellipsoid which, as a function of the dimensioning, has a favourable effect on the intensity transmission of the ellipsoid.

Reflector 18 produces a bundle of rays directed perpendicular to opening 15. It is conceivable that by arranging such reflectors within the ellipsoid (they can also be planar reflectors) the intensity transmission of the ellipsoid can be improved.

Light modulator 20 is symbolically shown in FIG. 1. It can either be a device for the periodic changing of the electric power at incandescent body 11 of FIG. 4 (technical modulation), or a rotary sector disk 21V ("Chopper") which, as shown in FIG. 10, is located in the path of the rays between light source 11 and detector 41.

Selective gas detection with an optical-spectroscopic method involves the use of monochromatic light. If an incandescent body is used as the light source and which naturally emits light in a wide spectral range, it is necessary to have a monochromator 30 (FIG. 1). However, a narrow-band interference filter is more suitable for our purposes. However, it is also conceivable to use a sealed cell filled with a suitable gas which, as a result of the specific absorption bands of the gas (mainly in the infrared spectral range is transparent in certain spectral ranges).

FIG. 11 shows the combination of a mechanical light modulator and a monochromator. At least one interference filter 33 or at least one gas cell 23 is arranged on rotary disk 32. If different interference filters 33, 33', 33'', etc or cells 34, 34', 34'', etc with different gas fillings, or combinations of interference filters and gas cells are used, it becomes possible to simultaneously separately detect several components of a gas mixture (further reference will be made to this hereinafter).

Instead of using round interference filters or gas cells, as shown in FIG. 11, it is conceivable to use sector-shaped, joined filter elements.

The spectroscopic detection of gases requires that the gas containing the component to be determined, hereinafter called the measuring gas, is located in the path of the rays between the light source and the detector. Fundamentally, this measuring gas can be introduced into the path of the rays at three different points, namely in the light source 10 of FIG. 1, between light source 10 and detector cell 40, or in detector cell 40. These three different cases will be considered in greater detail hereinafter.

In the first case, the measuring gas is introduced into the light source 10, i.e. into ellipsoid reflector 14. Reference is made in this connection to Swiss patent application No. 6 901/81-3 of Oct. 29, 1981.

The determination of the gas concentration is based on an extinction measurement, i.e. the determination of the attenuation of the light intensity by the wavelength of the absorption range of the measuring gas in the path of the rays. In this case, the reflector firstly acts as a light condenser, which supplies the light in bundled manner to the detectors and secondly acts as a multiple reflection cell. Detector 41 at 15 must be adapted to the absorption spectrum of the measuring gas in reflector 14. This can either be achieved by a photoacoustic cell 41 containing gas of the type to be determined, or through the use of a combination of an optical narrow-band filter 31 and a wide band detector 43, as shown in FIG. 12. Since, as stated, the gas concentration measurement is determined from the attenuation of the light intensity, it is absolutely necessary to carry out a measurement of the light beam not attenuated by the measuring gas, i.e. a so-called reference measurement. This reference measurement can e.g. be performed in that the light intensity is determined before it enters the absorption cell, which can obviously not be used in the present case. Alternatively, a light intensity measurement can be performed outside the spectral absorption range of the measuring gas. Such a reference measurement can either be performed with the aid of a spectrally selectively operating photoacoustic cell 41' in FIG. 13, or with a wide-band detector 43' with an optionally incorporated narrow-band filter 31'. Naturally, the absorption ranges of the measuring gas and the sensitivity range of the reference signal detector 41' or 43' must not overlap.

However, it is advantageous if the two detectors are operated in similar spectral ranges. In this way, it is possible to take account of the spectral behaviour of the reflectivity of the reflector 14 resulting from dirtying. This can be made possible by selecting the spectral transmission range of filter 31', or by introducing a suitable gas into photoacoustic cell 41' which does not occur in the measuring gas and which does not have any overlapping spectral bands with the latter.

The most frequently used method for measuring the spectral absorptivity involves placing the measuring gas in the path of the rays between light source 10 and detector cell 40, referred to as the second case hereinbefore.

A more detailed description will now be provided of a special arrangement of this type, namely non-dispersive gas analysis. The construction of such a gas analyzer is shown in simplified form in FIG. 14, in which 11 is the non-monochromatic radiation source. The light is split into two partial beams by reflector arrangement 19 and they in turn pass through the measuring gas cell 44 and reference cell 44'. The photoacoustic cell comprises the chamber 45 filled with the gas of the component under investigation, the light absorber 46, which absorbs all the radiation passing through chambers 44, 44', and the pressure difference measuring cell 47 containing the microphone diaphragm. The system operates in the following manner. From the continuous spectrum of light source 11, a small fraction is absorbed by the component under investigation with spectrum 103 in test gas chamber 44. The transmitted light is slightly reduced in this area, as is shown by curve 101 in FIG. 15. Account is also taken of the interference spectrum 105 by the gas component with overlapping spectrum, together with the spectrum 104 of another gas component in the test gas, e.g. carbon dioxide. The transmission of the reference cell containing e.g. gas of the interfering component with spectrum 106, is shown in 102. As the acoustic cell is filled with gas of the component under investigation, e.g. carbon monoxide, light is only absorbed in the chamber system in the range of spectrum 103. Due to the difference measuring method, the transmission spectrum 101 in range 103 is compared with the corresponding range of 102. Gas components with a spectrum 104 not overlapping with that of 103 can therefore give rise to a microphone signal. However, it is pointed out that this is not completely the case with the aforementioned system of carbon monoxide and carbon dioxide. If there is a partial overlap of the spectra, such as interference spectrum 105 and spectrum 103, a partial compensation by the reference gas with spectrum 106 is possible, but a so-called transverse influencing cannot be completely excluded.

A non-dispersively operating photoacoustic device can be constructed with the aid of an ellipsoid reflector, as shown in FIG. 16. Incandescent bodies 11 and 11' are located at the focal points. Light is coupled out through openings 15 and 15' along the main axis of the rotation ellipsoid 14. At mirrors 19, 19' and 19", 19"', the light bundles are deflected and supplied to cells 14 and 44'. The measuring gas to be investigated is located in cell 44, whilst cell 44' contains e.g. a reference gas.

The photoacoustic cell filled with the gas of the component under investigation comprises absorber 45 and detector 47. The outer chambers of 45 are connected to detector 47. The pressure difference between these chambers 45 resulting from the light absorption is detected by the microphone diaphragm in cell 47. In the central part of 45, there is an absorber 46, which completely absorbs the infrared light passing through the two outer chambers.

The equalizing of the light intensity at openings 15, 15' can be brought about by varying the luminosity of sources 11, 11'. There can possibly be an automatic equalizing, e.g. by means of infrared photodetectors incorporating semireflecting mirrors 19, 19'.

The third case of the measuring gas arrangement in the path of the rays will be discussed. A realisation of the measuring gas-filled detector cell 40 is based on the aforementioned photoacoustic effect. FIG. 17 shows the construction of the gas detection system according to the invention. Reference is made in this connection to Swiss Patent Application No. 2 058/81-9 of Mar. 26, 1981. The radiation of the e.g. thermally modulated incandescent body 11 is collected by means of reflector system 13, preferably a closed ellipsoid reflector 14 with coupling out of light along the large main axis, and is supplied to a narrow-band filter 31 under a small angular aperture of the light cone. The pass band of the filter is adapted to the absorption spectrum of the gas component to be detected, as illustrated in FIG. 18 with area B for a gas with absorption spectrum 103. It is pointed out that, unlike when using a laser where the light source is matched to a single rotation line, e.g. $A_i$, as a result of the band width of the filter the complete rotation structure is determined. This has a favourable effect on the absorbable quantity of light of the source which has in any case a low intensity. In the gases which absorb infrared radiation in several spectral ranges, it is necessary to select that range where on the one hand the absorption is at a maximum level and on the other where minimum importance is attached to the overlap with absorption spectra of other possible gas components as shown e.g. with spectrum 105 in FIG. 18. For the above reason, it may well be appropriate to only tune the filter to a partial zone C of the vibration-rotation structure. In the case that an interference filter 33 is used, a fine adjustment of the pass band can possibly be brought about by the oblique positioning thereof in the path of the rays. However, the interference with the measurement by other gas components can be largely eliminated e.g. by using more than one narrow-band filter adapted to the maxima or flanks of the measuring gas or interfering components. The effective gas concentration or the concentrations of the different components can then be digitally determined from the measurements performed with the different narrow-band filters 31, as described by P. Perlmutter, S. Shtrikman and M. Slatkine in Applied Optics, Vol. 13, p. 2267, 1979 for a device with a laser light source. The narrow-band filters can e.g. be successively introduced into the path of the rays. This can be performed in a simple manner by arranging them on a rotary disk, as shown in FIG. 11. As stated hereinbefore, this device can be simultaneously used for light modulation purposes. However, it is also possible to supply several filtered light bundles to the same photoacoustic cell 41, or to use several photoacoustic systems comprising a source 11, optics 13, filter 31 and cell 41, the filter in each system being adapted to a different gas component. The actual photoacoustic cell is a small and substantially closed cavity. Microphone 48 is fitted laterally. On the side facing the light entry window 49, there is a planar window 42, which can also have a curved configuration. The cell is not operated in acoustic resonance, particularly due to working at a low light modulation frequency.

Particular importance is attached to circulation of the measuring gas. The corresponding devices are designated by blocks 60 and 70 in FIG. 1. The gas exchange device relates to the light source 10 filled with the measuring gas, whilst 70 represents the corresponding unit for the measuring gas in detector cell 40.

In the first case of light source 10 filled with measuring gas, two problems occur. Firstly, the ellipsoidal shape makes efficient gas exchange more difficult and secondly it is necessary to ensure that gas flow fluctuations do not significantly vary the temperature and consequently the radiation intensity of the incandescent body light source 11. As glass is not transparent in the carbon dioxide absorption range and as other materials only have a limited suitability, it is virtually impossible to encapsulate the incandescent body in a bulb.

A uniform forced gas circulation, as shown in FIG. 19, is therefore advantageous. There are two additional openings 61, 61', together with a gas supply device 62 in the ellipsoid. This uniform and efficient gas circulation can e.g. be achieved by means of a small diaphragm pump.

For example, FIG. 20 shows a possible construction of a gas supply device 62, which could be suitable for air circulation. It is in fact a supply device produced by using a small loudspeaker 63 with plastic diaphragms with a diameter of 3 cm. 64 is the inlet valve and 64' the outlet valve - thin rubber diaphragms. For example, with an operating frequency of 50 Hz an air quantity of 0.7 cm$^3$/sec can be supplied counter to an overpressure of 5 mbar. The loudspeaker diaphragm is largely passivated against gas adsorption and therefore falsifications of the gas composition, in that a coating of aluminium is applied thereto by evaporation. Such a pump has operated continuously and in trouble-free manner for 10 months. An even better suppression of flow functions, as required e.g. if the light source 11 is to be thermally modulated, so that it must have a low thermal inertia, can be achieved if the partial area of the ellipsoid containing the incandescent body 11 is separated from the remaining reflector area by at least one thin diaphragm 65, 65' transparent to the particular radiation wavelength, or a thin tube 66, in the manner shown in FIG. 21. A particular problem arises if the measuring gas contains impurities, which can easily be deposited on the reflector surface in the form of dirt or condensate (e.g. water) and can therefore impair its reflectivity. In this case, it is advantageous to supply the measuring gas through a thin tube 66, which is transparent to the radiation in question and whose axis mainly falls in the focus 11' free from the light source. Such a construction is shown in FIG. 22.

In the case of the non-dispersive photoacoustic gas analyzer, as shown in FIGS. 14 and 16, no problem is encountered in connection with gas exchanger in the measuring gas cell 44. However, gas precleaning may be necessary. A feed device of the type shown in FIG. 20 may well be suitable for gas circulation.

The situation is more difficult in the case of a photoacoustic detection cell 40 filled with the measuring gas. Apart from the function of an efficient gas exchanger, device 70 must then also fulfil the acoustic cutout function.

During the measurement, it must on the one hand be ensured that the light absorption-dependent noise signal is not weakened by the escape of gas from the photoacoustic cell and on the other hand the penetration of external space noise, which could increase the noise level of the measurement must be prevented.

As in any case efficient gas exchange is linked with pressure fluctuations, measurement cannot take place during this time. Unlike in the cases of measuring gas-filled light source 10 or non-dispersive gas detected according to FIGS. 14 and 16, measuring gas must now be replaced in alternating operation with the aid of device 70, or the measuring detector cell must be kept acoustically sealed during the measurement.

Five possible solutions are considered and reference will now be made to these.

It is firstly possible to complete gas exchange by permanently open capillaries 71 in the detector cell wall. They must be kept so thin that acoustic decoupling is ensured during the measuring phase. Reference is made in this connection to FIG. 17. It has been found that capillaries with a diameter of about 0.1mm and a length of 0.5 mm adequately deaden the photoacoustically produced noise signal, but that an additional sound absorber 72 is required for preventing the coupling in of extreme noise. Such a construction is shown in FIG. 23, the sound absorber being constructed by means of cavities 73 and further capillaries 71. The thin capillaries 71 on the one hand and the additional cavities 73 on the other do not, however, permit a rapid gas replacement. The compression ratio of the gas feed device 62 of FIG. 20 is not adequate to satisfy this requirement, a more powerful pump 74 being required.

Two other possibilities of acoustic decoupling are described in Swiss Patent Application No. 4 853/81-8 of July 24, 1981 and are based on hydrodynamic acoustic decoupling.

FIG. 24 shows one of the possibilities. Pump means 62 draws the gas outside the system via supply line 74 through liquid medium 75 into container 76, from where it passes to photoacoustic cell 41 via connection 74". The gas displaced from photoacoustic cell 41 passes via connection 74''' through liquid medium 75' into container 76', where it is pumped out via supply line 74'.

If pump means 62 is out of operation, the photoacoustic cell is largely decoupled from the outside due to the liquid media 75 and 75', i.e. the photoacoustic signal is hardly attenuated and the penetration of acoustic spurious signals is largely prevented. The acoustic decoupling of the photoacoustic cell is based on the fact that the air and liquid media have very different sound hardnesses ($h = \sqrt{E \cdot p}$ E : modulus of elasticity, p: density) and therefore the acoustic power adaptation at the gas - liquid and liquid - gas intersections is very poor. For example, in the human ear, where this problem occurs in the case of sound transmission from the outer ear to the fluid in the inner ear, a good power adaptation is ensured by the auditory ossicles in the middle ear. Account is taken of the different sound hardness of air and ear fluid by a mechanical transmission (transmission ratio 60:1).

Due to the gas which only flows in surge-like manner as a result of the liquid media 75, 75', characteristic modulated pressure fluctuations occur in the photoacoustic cell 41 during the operation of pump means 62 and they are recorded by microphone 48. The resulting microphone signal makes it possible to check the function of the through-flow system.

The liquid media 75, 75' simultaneously act as a gas filter and make it possible to wash the gas before it enters the photoacoustic cell 41. By appropriate choice of media 75, 75', certain measurement-impairing components (e.g. $H_2O$) can be removed from the gas to be measured. For this purpose, it is also conceivable to connect by feed lines 74, 74' container 76, 76' to other identical containers and other gas treatment installations. For the purposes of an additional gas precleaning, media 75 and 75' can be replaced by solid substances.

To prevent liquid media 75, 75' from penetrating the interior of the optoacoustic cell, the device must be correctly positioned with respect to the gravity, as shown in FIG. 24.

If the device is located in a reference system with a time-variable polar vector of gravitation $\vec{g}$, it is for example mounted by gimbal-like means. This measure to a certain extent compensates position variations, the limits being set by the necessary connections. Instead of connecting pump means 62 at 74', as shown in FIG. 24, it can also be positioned at 74.

FIG. 25 shows an additional measure enabling containers 76, 76' to be connected by means of feed lines 77 to one or more containers 76", e.g. below the liquid media 75, 75', said container 76" containing stocks of media 75, 75', so that after a certain time, said media can be automatically changed in 75, 76', e.g. by means of valves 77'. This method is particularly suitable when using several measuring cells.

FIG. 26 shows a further embodiment of the invention. Liquid media 75, 75' are located in capillaries 78, 78'. The diameters of capillaries 78, 78' are dimensioned in such a way that with identical pressure in expansion containers 78" or 78''' and in outlet connections 78IV or 78V the capillary forces prevent an outflow of liquid medium 75 at around the operating temperatures.

In outlet connection 78V, pump means 62 produces such a pressure drop that the liquid medium 75 escapes out of capillaries 78 into expansion container 78" and the gas in outlet connection 78IV passes via capillary 78 into expansion container 78" and via feed lines 74" into photoacoustic cell 41.

The gas displaced from photoacoustic cell 41 passes via feed line 74''', into expansion container 78''', where it forces the medium 75' in capillary 78' into outlet connection 78V and evacuates it.

If pump means 62 is switched off, the liquid medium 75 or 75' in expansion container 78" or outlet connection 78V respectively flows back into capillaries 78, 78' respectively and decouples the photoacoustic cell 41 from external space noise sources and simultaneously ensures the deadening of the photoacoustic pressure signal in the cell. Instead of fitting pump means 62 at outlet connection 78V, it can be fixed to outlet connection 78IV.

To prevent media 75, 75' from penetrating cell 41 and to ensure the return flow into the corresponding capillaries, in the case of the presently described arrangement, the cell only has to be correctly mounted relative to gravity during the gas exchange phase, as shown in FIG. 26. Outside the gas exchange phases, e.g. during transportation, measurement, etc., no importance is attached to the mounting position, due to the capillary forces acting during these intermediate phases, because they prevent the outflow of media 75, 75'.

Here again, the function of the through-flow device during the gas exchange can be checked by microphone 48, due to the resulting characteristic modulated pressure fluctuations in photoacoustic cell 41.

A fourth possibility of acoustic decoupling is provided by small balls 79 which, as a result of gravity, are pressed against valve seat 79', of FIG. 27. Such ball valves are located on either side of the photoacoustic cell. The efficiency of pump means 62 (according to FIG. 20) must satisfy the set requirements regarding compression and gas circulation time.

A fifth construction of a gas exchange cutout device is shown in FIG. 28. It is a combination of a gas feed device, as shown in FIG. 20, and a plate valve. During the gas exchange phase, both gas feed devices 62, 62' are in the feed state, i.e. the loudspeaker diaphragms 66, 66' with valve plates 65, 65' vibrate. During the measuring phase, the two loudspeaker diaphragms 66, 66' are controlled in such a way that the valve plates 65, 65' are pressed against valve seats 67, 67'. The hoods or domes 68, 68' reduce the transmission of space noise via the loudspeaker diaphragms.

In connection with the detection and processing of the electrical signals of detectors 40 or 50 and the control of light modulator 20 and optionally monochromator 30 and gas exchanger 70, a device 80 is required.

A combined control and lock-in amplifier system was firstly constructed with the aid of a Rockwell AIM 65 microcomputer. The block diagram of the hardware part, without pump control, is shown in FIG. 29. 81 is the low-noise preamplifier, which accepts the signals, e.g. from an electret microphone with integrated input amplifier. The signal is then supplied to a band pass filter 82 with a relatively low Q-factor, which frees the same from the low and high frequency part of the noise. This filtering is necessary, because the dynamic range of a digitally functioning lock-in amplifier is limited, i.e. the digitizing stage 84 must not be subject to unnecessary noise. Prior to digitizing in the voltage-frequency converter 84, the signal is brought into the voltage range favourable for 84 in an amplifier stage 83 controlled by microcomputer 85. The incandescent body, i.e. the light source is controlled by an internal oscillator of the microcomputer by means of a power amplifier 86. The measuring process is started by means of a starting device 87.

The software construction of the microcomputer system is shown in FIG. 30 by means of a highly simplified flow chart. Following start 91, initially the complete system is initialized 92, i.e. the multichannel stores are organized, the internal oscillator for light modulation started and the optimum amplification of stage 83 determined. This is followed by the accumulation 92 of the voltage-frequency converter pulses in the multichannel store. The amplified and pulse-converted microphone signal is summated in the multichannel store during a predetermined number of cycles of the internal oscillator and consequently so is the light modulation. This accumulation is accurately synchronized with the internal oscillator. At the end of the accumulation, the content of the multichannel store is correlated with a precisely symmetrical, square-wave signal with the cycle of the light modulation 94. The phase of the square-wave signal with respect to the accumulated values is displaced until the result of the correlation is optimum. As the phase position between the microphone signal and the reference was found to be largely independent of the gas concentrations in the optoacoustic cell 41, there is no need to reset the phase on each occasion and can be incorporated as a constant. With the optimization condition fulfilled, the r.m.s. value and the microphone signal phase with respect to the light modulation is found as a reference and the data output 95 can be carried out. The programme is then either interrupted 96 or recommenced in accordance with a time plan. No account is taken of the control of the gas change in this flow chart. As is apparent, the system operates on an off-line basis, i.e. firstly the accumulation is carried out and only then is the measuring signal correlated with the reference signal. This procedure is undesired if the time pattern of a quantity is to be constantly followed. In our case, where the measurement is in any case discontinuous due to the gas and possibly interference filter change, preference is given to the described system because it makes it possible to start measurement immediately after fixing the operating parameter. This fact is particularly important if several photoacoustic systems 111–115 are to be simultaneously or sequentially controlled with a single control unit 80, as illustrated in FIG. 31. In the latter, the detection systems 111 and 112 are connected in parallel, as are units 113, 114. The parallel connection means that the particular cells 41 are simultaneously scavenged by means of the feed device 62 and the light sources 11 are operated synchronously. Thus, the accumulation of the microphone signals must also take place simultaneously by means of separate interfaces of microcomputer 80.

The combined systems 111, 112 and 113, 114, as well as the individual system 115 are dealt with sequentially in our example. The following sequence is conceivable. During the performance of the accumulation of microphone signals of 111 and 112, the gas is replaced in the optoacoustic cells 41 of units 113, 114. Simultaneously, the previously accumulated signal of unit 115 is correlated and the result is directly indicated or with respect to a threshold value.

We claim:
1. An optical detection system for selectively detecting gas, comprising:
   a light source including an emitter and an ellipsoid reflector shaped as a rotation ellipsoid with a major axis and surrounding two focal points of said ellipsoid, said emitter being located within said reflector adjacent one of said focal points, said reflector having at least one small opening on said major axis for emitting a high intensity light bundle parallel to said major axis;
   a gas collecting cell in an optical path of said light source;
   a light modulator coupled to said light source;
   detector means for generating signals representative of gases detected from light emitted from said gas collecting cell;
   a monochromator between said light source and said detector means; and
   signal processing means, coupled to said detector means, for analyzing the signals of said detector means.

2. An optical detection system according to claim 1 wherein said gas collecting cell is in said reflector.

3. An optical detection system according to claim 1 wherein said gas collecting cell is in said detector means.

4. An optical detection system according to claim 1 wherein said reflector is widened to form said opening.

5. An optical detection system according to claim 4 wherein a concave reflecting member is spaced from said ellipsoid reflector on an extension of said major axis, at least one focal point of said reflecting member coinciding with one of said focal points of said ellipsoid reflector.

6. An optical detection system according to claim 4 wherein a concave mirror is mounted in said ellipsoid reflector on said major axis, said concave mirror having a focal point coinciding with one of said focal points of said ellipsoid reflector.

7. An optical detection system according to claim 4 wherein measuring gas is inside said ellipsoid reflector; and a cell-like chamber in said ellipsoid reflector isolates said measuring gas from said emitter.

8. An optical detection system according to claim 4 wherein said ellipsoid reflector comprises a second opening forming a reference light outlet.

9. An optical detection system according to claim 4 wherein said gas collection cell is located in said detector means to receive modulated measuring light from said modulator and comprises a light beam emanating area, said gas collection cell having gas supply means coupled thereto and microphone means, positioned adjacent said light beam emanating area, for receiving photoacoustic effects.

10. An optical detection system according to claim 9 wherein said gas collection cell comprises a gas exchange device with a capillary extending into said gas collection cell at one end thereof and coupled to said gas supply means at another end thereof.

11. An optical detection system according to claim 9 wherein said gas collection cell comprises a gas exchange device including a capillary with one end extending into said gas collection cell and another end coupled to a gas port, said capillary having a sound absorber and means for remaining open during measuring phases.

12. An optical detection system according to claim 9 wherein said gas collection cell comprises an inlet and an outlet, said inlet and said outlet having first and second barrier fluids, respectively, thereat.

13. An optical detection system according to claim 12 wherein barrier fluid containers are mounted at said inlet and outlet, and lines extending from said inlet and said outlet are immersed in said barrier fluids.

14. An optical detection system according to claim 12 wherein said barrier fluids are contained in barrier fluid capillaries located adjacent said inlet and said outlet.

15. An optical detection system according to claim 13 wherein a storage container housing additional barrier fluids is in fluid communication with said barrier fluid containers through a barrier fluid line to supply additional fluids thereto.

16. An optical detection system according to claim 15 wherein said barrier fluid line comprises valve means for controlling fluid flow into said barrier flow containers.

17. An optical detection system according to claim 14 wherein said barrier fluid capillaries are coupled at ends thereof to expansion vessels by funnel-shaped, continuously widening portions for successively reducing capillary action.

18. An optical detection system according to claim 9 wherein said gas supply means comprises at least one loudspeaker and a valve seat, said loudspeaker having a diaphragm with a valve plate coupled thereto and movable toward and away from said valve seat.

19. An optical detection system according to claim 1 wherein said light modulator comprises a rotatable disk in said optical path, said disk having openings receiving band pass filters.

20. An optical detection system according to claim 1 wherein said light modulator comprises a rotatable disk in said optical path, said disk having openings receiving gas filled cells.

21. An optical detection system according to claim 9 wherein said gas collection cell comprises an optoacoustic measuring cell; and said microphone means senses characteristic pressure fluctuations produced in said measuring cell during gas exchanges, and generates and transmits electrical signals to control means for regulating operation of the system.

* * * * *